United States Patent
Legl et al.

(10) Patent No.: US 7,553,071 B2
(45) Date of Patent: Jun. 30, 2009

(54) SENSOR UNIT

(75) Inventors: Stefan Legl, Leinfelden-Echterdingen (DE); Gerold Stauss, Herrenberg (DE)

(73) Assignee: Sitronic Gesellschaft für Elektrotechnische Ausrüstung mbH & Co. KG, Gärtringen (DE)

( * ) Notice: Subject to any disclaimer, the term of this patent is extended or adjusted under 35 U.S.C. 154(b) by 217 days.

(21) Appl. No.: 10/556,917

(22) PCT Filed: Mar. 6, 2004

(86) PCT No.: PCT/DE2004/000445

§ 371 (c)(1),
(2), (4) Date: Sep. 1, 2006

(87) PCT Pub. No.: WO2004/104523

PCT Pub. Date: Dec. 2, 2004

(65) Prior Publication Data

US 2007/0017307 A1    Jan. 25, 2007

(30) Foreign Application Priority Data

May 16, 2003    (DE) .............................. 103 22 017

(51) Int. Cl.
*G01N 25/66* (2006.01)
*G01D 21/02* (2006.01)
*G01D 11/24* (2006.01)
*G01D 11/26* (2006.01)
*G01D 5/12* (2006.01)

(52) U.S. Cl. .................. 374/28; 73/335.02; 73/866.1; 374/142

(58) Field of Classification Search ............ 73/866.12, 73/29.01, 335.02, 866.1; 374/28, 142
See application file for complete search history.

(56) References Cited

U.S. PATENT DOCUMENTS

| | | | |
|---|---|---|---|
| 3,548,633 A | 12/1970 | Webb | |
| 5,094,109 A | 3/1992 | Dean et al. | |
| 5,257,547 A | 11/1993 | Boyer | |
| 5,381,604 A * | 1/1995 | Heidel et al. | 33/366.21 |
| 5,396,796 A | 3/1995 | Kotani et al. | |
| 5,511,320 A * | 4/1996 | Heidel et al. | 33/366.13 |
| 5,703,754 A * | 12/1997 | Hinze | 361/736 |
| 5,932,875 A | 8/1999 | Chung et al. | |
| 6,028,773 A * | 2/2000 | Hundt | 361/760 |
| 6,344,791 B1 | 2/2002 | Armstrong | |
| 6,354,153 B1 | 3/2002 | Weiblen et al. | |
| 6,546,800 B1 * | 4/2003 | Namerikawa et al. | 73/514.34 |
| 6,580,077 B2 * | 6/2003 | Ito et al. | 250/338.3 |
| 6,990,847 B2 * | 1/2006 | Happach | 73/29.02 |

FOREIGN PATENT DOCUMENTS

| | | | |
|---|---|---|---|
| DE | 199 14 469 C1 | 6/2000 | |
| DE | 693 27 859 T2 | 7/2000 | |
| EP | 142827 A1 * | 5/1985 | 340/577 |
| EP | 296634 A2 * | 12/1998 | 340/628 |
| JP | 55035222 A | 3/1980 | |
| JP | 64002220 A | 1/1989 | |
| JP | 07191116 A | 7/1995 | |
| JP | 11288803 A * | 10/1999 | |
| WO | WO 92/10731 A1 | 6/1992 | |
| WO | WO 93/11414 A1 | 6/1993 | |
| WO | WO 02/33395 A | 4/2002 | |

* cited by examiner

*Primary Examiner*—Thomas P Noland
(74) *Attorney, Agent, or Firm*—Walter A. Hackler

(57) ABSTRACT

A sensor unit (1) comprises at least one sensor (3) that is arranged on a circuit board (2) and a cover (4) for the sensor (3). The cover (4) is open toward the circuit board (2) and adjoins the circuit board (2) in the installed state. The underside (14) of the circuit board simultaneously forms part of the seal. The at least one sensor (3) is completely climate-encapsulated.

1 Claim, 1 Drawing Sheet

SENSOR UNIT

The invention pertains to a sensor unit with at least one sensor that is arranged on a circuit board and provided with a sensor cover.

A sensor unit of this type is known, for example, from WO 02/33395 A1.

This known sensor unit contains a hygrometric sensor for measuring the relative humidity and a thermometric sensor for measuring the air temperature. If air with a certain absolute humidity is cooled, the relative humidity increases until it reaches a value of 100%. The temperature at which the relative humidity reaches 100% is referred to as the condensation point or dew point. Water condensation takes place if the temperature decreases further or the absolute water content increases. The dew point can be calculated from the measured relative humidity and the measured air temperature. Sensor units of this type are used in numerous technical fields, particularly as a protection against fogging.

According to WO 02/33395, a climate encapsulation may also be attached to the circuit board in order to protect the sensor unit from environmental influences. This climate encapsulation may be manufactured of a material that is pervious to the atmosphere on one or both sides. If only one side of the encapsulation is pervious to the atmosphere, the second protective element can be manufactured of any material that is impervious to the atmosphere.

The applicant aims to improve the encapsulation or seal of the at least one sensor arranged on the circuit board.

SUMMARY OF THE INVENTION

This objective is attained with a sensor unit with at least one sensor that is arranged on a circuit board and provided with a sensor cover, wherein the cover is open toward the circuit board and adjoins the circuit board when it is mounted thereon, and wherein the underside of the circuit board simultaneously forms part of the seal. The circuit board is utilized as part of the seal and integrated into the encapsulation of the at least one sensor. Due to its special constructive design, the underside of the circuit board simultaneously fulfills a sealing function such that the sensors are completely climate-encapsulated. In this context, the term constructive design refers to the circuit board containing a bore, a cavity or a blind hole of arbitrary cross section. The element of the sensor that is sensitive to humidity is arranged above this bore or the like that, however, is not realized in the form of a through-bore.

A sealing lip can be used in order to realize a correspondingly optimized seal. This seal can be additionally improved if the sealing lip extends along the periphery of the cover.

In order to simplify the installation of the cover, the circuit board is provided with a peripheral groove for inserting a lower edge of the cover. The position of the cover is predetermined in this fashion, and the cover can be pre-fixed in this position.

If the sensor unit is intended for determining the relative humidity, the cover contains a wall section and a membrane that is pervious to the atmosphere, particularly the atmospheric humidity, and connected to this wall section.

In order to realize the attachment and/or insertion of the cover on/into the circuit board, the cover may be provided with legs and the circuit board may be provided with bores for inserting the legs.

Although not exclusively designed for this purpose, the invention is particularly suitable for use in connection with a sensor unit for determining the dew point that comprises a hygrometric sensor and a thermometric sensor.

BRIEF DESCRIPTION OF THE DRAWINGS

One embodiment of the sensor unit according to the invention is schematically illustrated in the figures and described below with reference to the figures. The figures show.

DETAILED DESCRIPTION

Figure 1:
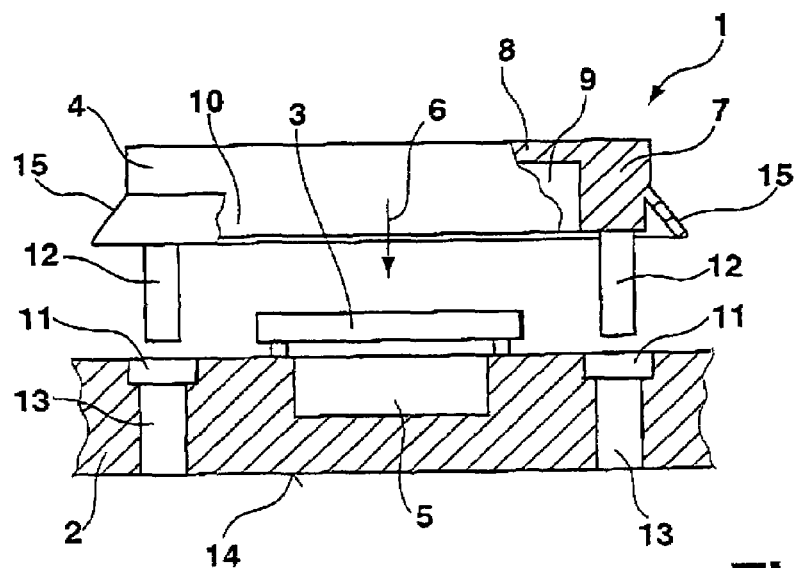
FIG. 1, a cross section through a sensor unit along the line of section I-I in FIG. 2, and FIG. 2, a top view of part of the sensor unit according to FIG. 1.
Figure 2:
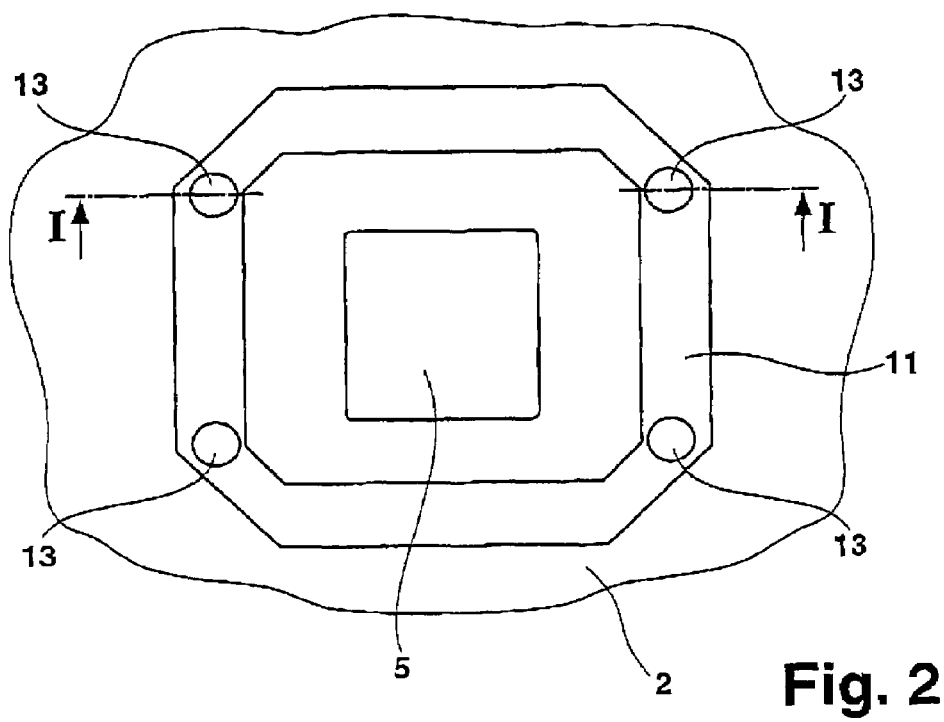

FIG. 1 shows that a sensor unit 1 for determining the dew point essentially comprises a circuit board 2 that serves as a mounting base, a hygrometric sensor 3, a thermometric sensor that is not shown in FIG. 1 and a cover 4 for covering the sensors. The sensors are integrated into an electric and/or electronic circuit via the strip conductors of the circuit board 2. A thermally conductive coating of the circuit board 2 also ensures that a superior heat transfer is achieved between the sensors and that no measurable difference in temperature occurs between the installation site of the thermometric sensor and that of the hygrometric sensor 3. The hygrometric sensor 3 serves for measuring the relative humidity. The thermometric sensor serves for measuring the temperature of the air to be analyzed. Other components arranged on the mounting base 1 are not illustrated in order to provide a better overview.

The hygrometric sensor 3 comprises two electrically conductive electrodes, between which a dielectric in the form of a polymer is arranged. The dielectric properties of the polymer are influenced by the relative humidity. The relative humidity and the water that is molecularly absorbed by the polymer are distinctly correlated. The thermometric sensor is realized in the form of a temperature-dependent resistor. Therefore, it is possible to calculate the dew point based on the results of the capacitance measurement of the hygrometric sensor 3 and the resistance measurement of the thermometric sensor.

The active side of the hygrometric sensor 3 is arranged above a recess or cavity 5 in the circuit board 2. The cavity 5 serves for uniformly exposing the largest surface of the hygrometric sensor 3 possible to the air mixture, i.e., essentially the entire active side of this sensor. In addition, the cavity 5 improves the air flow in cooperation with corresponding slots in the housing of the sensor unit. This makes it possible to direct the flow of air to be analyzed toward the hygrometric sensor 3. The constructive design of the cavity is realized in such a way that the underside 14 of the circuit board is simultaneously utilized as part of the seal. Any feedthroughs required for the strip conductors within the sealing region of the circuit board are soldered shut during the component soldering process.

The hygrometric sensor 3 and the thermometric sensor can be protected by means of the cover 4 by placing the cover 4 over the sensors in the installation direction 6. The cover 4 contains a peripheral wall section 7 and a membrane 8 that is pervious to the atmosphere and preferably has a self-cleaning surface. The hollow space 9 between the wall section 7 and the membrane 8 serves for accommodating the sensors. The wall section 7 has a thickness that makes it possible to insert the lower edge 10 of the wall section 7 into a peripheral groove 11. The groove 11 defines the installation position and makes it possible to pre-fix the cover 4 in this position. The wall section 7 is connected to four legs 12 that can be inserted into bores 13. In the inserted state, the legs 12 slightly protrude over the underside 14 of the circuit board 2 and can be additionally fixed by means of hot-pressing. A peripheral sealing lip 15 formed on the wall section 7 slightly protrudes over the cover 4 in the direction of the circuit board 2 and adjoins the circuit board 2 in the attached state of the cover 4. This is achieved by bending the sealing lip 15 of elastic plastic material outward such that it subsequently adjoins the circuit board with a slight prestress. This ensures a climate-compatible seal for this type of application. The cover 4 therefore fulfills a climate encapsulation function.

LIST OF REFERENCE SYMBOLS

1 Sensor unit
2 Circuit board
3 Hygrometric sensor
4 Cover
5 Cavity
6 Installation direction
7 Wall section
8 Membrane
9 Hollow space
10 Edge of wall section
11 Groove
12 Leg
13 Bore
14 Underside of circuit board
15 Sealing lip

The invention claimed is:

1. A sensor unit comprising:

at least one sensor disposed on a circuit board;

a sensor cover, said cover sensor being open toward the circuit board and adjoining the circuit board when installed with an underside of the circuit board forming a part of a seal therebetween;

a sealing lip extending along a periphery of the cover for adjoining and sealing with the circuit board with a preselected stress;

a recess or blind hole in said circuit board beneath the sensor;

a peripheral groove in said circuit board for inserting a lower edge of the cover;

a wall section and a membrane, disposed in the cover, said membrane being pervious to the atmosphere and connected to a wall section of the cover;

legs disposed on the cover and bores, disposed in said circuit board, for receiving the legs; and a hygrometric sensor and a thermometric sensor for determining a dew point.

* * * * *